United States Patent [19]

Fochler

[11] Patent Number: 5,326,305
[45] Date of Patent: Jul. 5, 1994

[54] PROTECTIVE BREAST PAD

[76] Inventor: Zhou Li Fochler, 301 Cathedral Pkwy., 14G, New York, N.Y. 10026

[21] Appl. No.: 942,504

[22] Filed: Sep. 10, 1992

[51] Int. Cl.$^5$ .............................................. A41C 3/14
[52] U.S. Cl. ...................................... 450/57; 450/37; 450/55; 450/81; 2/56; 2/58; 2/267
[58] Field of Search ....................... 2/67, 73, 267, 268, 2/53, 54, 55, 56, 57, 58; 450/31, 32, 37, 38, 55, 56, 57, 81; 604/385.1, 389, 386, 390, 383, 387; 602/58; 128/888; 623/7, 8

[56] References Cited

U.S. PATENT DOCUMENTS

| | | | |
|---|---|---|---|
| 1,108,427 | 8/1914 | Brennan | 2/53 |
| 2,344,781 | 3/1944 | Mullen | 2/53 |
| 3,280,818 | 10/1966 | Pankey et al. | 450/81 |
| 3,356,090 | 12/1967 | Plantinga et al. | 450/37 X |
| 3,588,916 | 6/1971 | Glatt | 2/53 |
| 4,047,534 | 9/1977 | Thomaschefsky et al. | 450/37 X |
| 4,100,621 | 7/1978 | Ettipio | 450/32 X |
| 4,747,162 | 3/1988 | Yanagihara | 2/53 |
| 4,856,111 | 8/1989 | Sholes | 2/56 |

Primary Examiner—Clifford D. Crowder
Assistant Examiner—Jeanette E. Chapman
Attorney, Agent, or Firm—Richard L. Miller

[57] ABSTRACT

A flat cushion sized to cover the breast of the woman has an adhesive layer applied to one side thereof, while a protective cover is applied over the adhesive layer. When the protective cover is pulled off, the adhesive layer can be pressed against the inner surface of a woman's garment to allow an opposite side of the flat cushion to cover the breast of the woman.

6 Claims, 1 Drawing Sheet

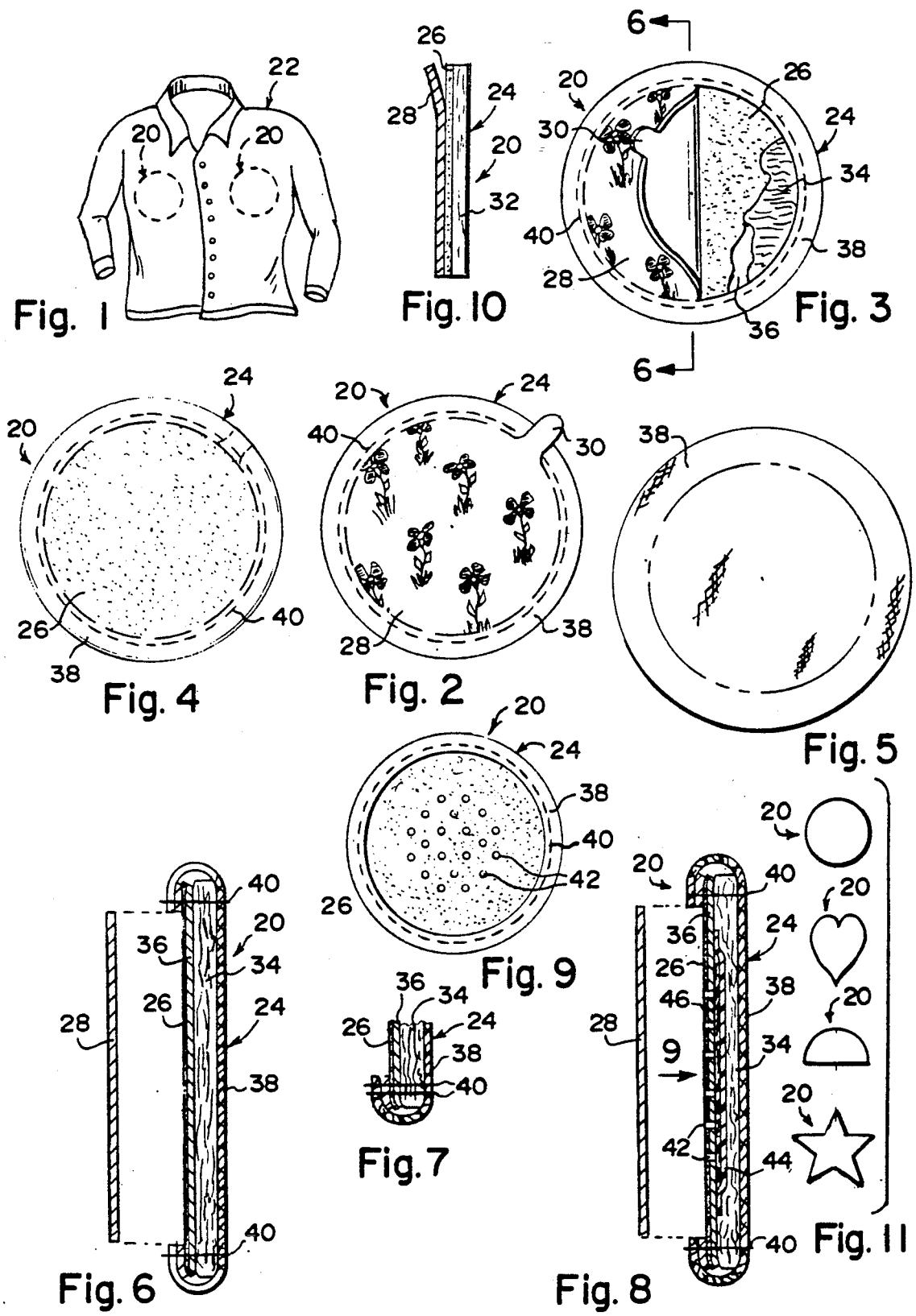

PROTECTIVE BREAST PAD

BACKGROUND OF THE INVENTION

The instant invention relates generally to breast pads and more specifically it relates to a protective breast pad.

Numerous breast pads have been provided in the prior art that are adapted to extend over the breasts of women. For example, U.S. Pat. No. 4,343,313 to Le Jeune; U.S. Pat. No. 4,398,981 to Ellis and U.S. Pat. No. 4,674,510 to Sneider all are illustrative of such prior art. While these units may be suitable for the particular purpose to which they address, they would not be as suitable for the purpose of the present invention as hereafter described.

SUMMARY OF THE INVENTION

A primary object of the present invention is to provide a protective breast pad that will overcome the shortcomings of the prior art devices.

Another object is to provide a protective breast pad that is removably attached to the inner surface of a woman's garment to be in a position to cover the breast of a woman, while allowing the breast to move freely with respect to the protective breast pad.

An additional object is to provide a protective breast pad that can be removably attached to the inner surface of the woman's garment by an adhesive layer which is protected by a removable protective cover.

A further object is to provide a protective breast pad that is simple and easy to use.

A still further object is to provide a protective breast pad that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

The figures in the drawings are briefly described as follows:

FIG. 1 is a diagrammatic perspective view illustrating the location of where the instant invention is placed in a woman's garment;

FIG. 2 is an elevational view of the instant invention per se before it is installed in a garment;

FIG. 3 is another elevational view, with parts broken away, similar to FIG. 2 further illustrating the adhesive protective cover being removed therefrom;

FIG. 4 is still another elevational view after the adhesive protective cover has been entirely removed and the instant invention is ready to be placed in a garment;

FIG. 5 is a diagrammatic view illustrating just the outer fabric sheet before it has been folded and sewed to the inner materials of the instant invention;

FIG. 6 is a cross sectional view taken on line 6—6 of the instant invention;

FIG. 7 is a cross sectional view, with parts broken away, taken on line 6—6 illustrating another stitching securement thereto;

FIG. 8 is a cross sectional view taken on line 6—6 of a second embodiment of the invention;

FIG. 9 is a view taken in the direction of arrow 9 in FIG. 8 after the adhesive protective cover has been entirely removed.

FIG. 10 is a cross sectional view of a third embodiment of the invention; and

FIG. 11 are elevational views showing different geometric shapes for the instant invention.

DETAILED DESCRIPTION OF THE PREFERRED EMBODIMENTS

Turning now descriptively to the drawings, in which similar reference characters denote similar elements throughout the several views, the Figures illustrate a protective breast pad 20 to be worn on an inner surface of a woman's garment 22 over a breast of a woman. The protective breast pad 20 consists of a flat cushion 24 sized to cover the breast of the woman. An adhesive layer 26 is applied to one side of the flat cushion 24. A protective cover 28 is applied over the adhesive layer 26. When the protective cover 28 is pulled off, the adhesive layer 26 can be pressed against the inner surface of the woman's garment 22, to allow an opposite side of the flat cushion 24 to cover the breast of the woman. The flat cushion 24, shown in FIG. 10, is typically a single sheet of thin soft cotton-like material 32.

The protective cover 28 contains an integral pull tab 30 at its edge, so that the protective cover 28 can be easily pulled off of the adhesive layer 26 by the pull tab 30. The flat cushion 24, as shown in FIGS. 2 through 7 includes an inner soft material sheet 34. A liner sheet 36 is placed against one side of the inner soft material sheet 34 to receive the adhesive layer 26. A slightly larger outer fabric sheet 38 is placed against an opposite side of the inner soft material sheet 34. Stitches 40 are placed about the edges of the outer fabric sheet 38 after the edges are folded over the edges of the inner soft material sheet 34 and the liner sheet 36.

The flat cushion 24, as shown in FIGS. 8 and 9, further includes the liner sheet 36 having a plurality of small holes 42 therethrough. A plastic sheet 44 is affixed to the back of the liner sheet 36 over the small holes 42 to form a pocket therein. A absorbant sheet 46 is retained within the pocked formed by the plastic sheet 44 to cover the small holes 42. The absorbant sheet 46 can contain a perfume saturated therein which is only released so that the scent is allowed to exude through the plurality of small holes 42 in liner sheet 36 when the protective cover 28 is pulled away and removed therefrom, while at the same time the inner soft material sheet 34 can receive and retain any perspiration or lactating fluids from the breast of the woman.

The protective breast pad 10 can be washable and reusable many times, or it can be disposable by being used only one time, depending upon what kind of materials are utilized in fabricating the flat cushion 24. It can have fancy decorations, be perfumed and come in different colors and sizes. The protective breast pad 10 can also come in different shapes as shown in FIG. 11, typically a circle, a heart, a semi-circle and a star. Other shapes not illustrated can also be made.

When worn by a women the instant invention 20 has the benefit of providing some protection from mechanical impact to the breast area while providing simultaneously more freedom from a restrained feeling of being harnessed into a conventional brassiere. Another benefit is when worn under rather sheer fabric garment the instant invention prevents nipples, their size and other personal associated body characteristics.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A protective breast pad to be worn on an inner surface of a woman's garment over a breast of a woman which comprises:
   a) a flat cushion sized to cover the breast of the woman;
   b) an adhesive layer applied to one side of said flat cushion; and
   c) a protective cover applied over said adhesive layer, so that when said protective cover is pulled off, said adhesive layer can be pressed against the inner surface of the woman's garment, to allow an opposite side of said flat cushion to cover the breast of the woman, wherein said protective cover includes an integral pull tab at its edge, so that said protective cover can be easily pulled off of said adhesive layer by said pull tab, wherein said flat cushion includes:
   i) an inner soft material sheet;
   ii) a liner sheet placed against one side of said inner soft material sheet and receiving said adhesive layer, said liner sheet having a plurality of small holes therethrough;
   iii) a slightly larger outer fabric sheet placed against an opposite side of said inner soft material sheet; and
   iv) stitches placed about the edges of said outer fabric sheet after the edges are folded over the edges of said inner soft material sheet and said liner sheet said liner sheet having a plurality of small holes therethrough;
   v) a plastic sheet affixed to the back of said liner sheet over said small holes to form a pocket therein; and
   vi) an absorbent sheet saturated with a perfume retained within the pocket formed by said plastic sheet to cover said small holes, so as to allow a perfume scent to exude through said small holes when said cover is pulled off.

2. A protective breast pad as recited in claim 1, wherein said flat cushion is a single sheet of thin soft cotton-like material.

3. A protective breast pad as recited in claim 1, which is disc shaped.

4. In combination, a woman's upper torso covering outer garment and a protective breast pad comprising a smooth, flat cushion sized to cover substantially only the breast of a woman wearing the garment and having a layer of pressure sensitive adhesive on one side thereof for adhering to the inner surface of the garment thereby attaching the breast pad to the garment so that the opposite side is located covering the breast of a woman wearing the garment, wherein said flat cushion includes:
   a) an inner soft material sheet;
   b) a liner sheet placed against one side of said inner soft material sheet and receiving said adhesive layer;
   c) a slightly larger outer fabric sheet placed against an opposite side of said inner soft material sheet;
   d) stitches placed about the edges of said outer fabric sheet after the edges are folded over the edges of said inner soft material sheet and said liner sheet;
   e) said liner sheet having a plurality of small holes therethrough;
   f) a plastic sheet affixed to the back of said liner sheet over said small holes to form a pocket therein; and
   g) an absorbent sheet saturated with a perfume retained within the pocket formed by said plastic sheet to cover said small holes, so as to allow a perfume scent to exude through said small holes.

5. A protective breast pad as recited in claim 4, wherein said flat cushion is a single sheet of thin soft cotton-like material.

6. The combination recited in claim 4, wherein the pad is of disc shape.

* * * * *